(12) United States Patent
Rusnak et al.

(10) Patent No.: US 6,844,561 B1
(45) Date of Patent: Jan. 18, 2005

(54) ROTATING APERTURE SYSTEM

(75) Inventors: Brian Rusnak, Livermore, CA (US); James M. Hall, Livermore, CA (US); Stewart Shen, Danville, CA (US); Richard L. Wood, Santa Fe, NM (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 239 days.

(21) Appl. No.: 10/284,175

(22) Filed: Oct. 31, 2002

Related U.S. Application Data

(60) Provisional application No. 60/330,877, filed on Nov. 1, 2001.

(51) Int. Cl.[7] .............................................. G21K 1/04
(52) U.S. Cl. .................................... 250/505.1; 250/251
(58) Field of Search ............................ 250/505.1, 251; 376/108, 116, 109, 115; 369/271

(56) References Cited

U.S. PATENT DOCUMENTS

| | | | |
|---|---|---|---|
| 4,008,411 A | * | 2/1977 | Brugger et al. ............. 376/117 |
| 4,757,209 A | * | 7/1988 | Kreissl et al. ............. 250/505.1 |
| 4,992,656 A | * | 2/1991 | Clauser ...................... 250/251 |
| 5,559,333 A | * | 9/1996 | Araya et al. ................. 250/344 |
| 5,677,534 A | * | 10/1997 | Araya ......................... 250/345 |
| 6,297,507 B1 | * | 10/2001 | Chen et al. ............. 250/370.11 |
| 6,619,842 B1 | * | 9/2003 | Artig et al. ................. 378/203 |

FOREIGN PATENT DOCUMENTS

| | | | | |
|---|---|---|---|---|
| GB | 2305290 A | * | 4/1997 | ............ H05H/3/06 |
| GB | 2305290 | | 4/1997 | .......... H05H/3/066 |

OTHER PUBLICATIONS

Brian Rusnak et al., "A Deuterium Accelerator for Neutron Radiography", Nov. 11, 2001, American Nuclear Society Winter Meeting, Reno, NV.

* cited by examiner

*Primary Examiner*—John R. Lee
*Assistant Examiner*—Johnnie L Smith, II
(74) *Attorney, Agent, or Firm*—William C. Daubenspeck; Paul A. Gottlieb

(57) ABSTRACT

A rotating aperture system includes a low-pressure vacuum pumping stage with apertures for passage of a deuterium beam. A stator assembly includes holes for passage of the beam. The rotor assembly includes a shaft connected to a deuterium gas cell or a crossflow venturi that has a single aperture on each side that together align with holes every rotation. The rotating apertures are synchronized with the firing of the deuterium beam such that the beam fires through a clear aperture and passes into the Xe gas beam stop. Portions of the rotor are lapped into the stator to improve the sealing surfaces, to prevent rapid escape of the deuterium gas from the gas cell.

47 Claims, 3 Drawing Sheets

ROTATING APERTURE SYSTEM

This application claims priority to Provisional Patent Application Ser. No. 60/330,877, titled "Accelerator For Neutron Radiography Having Improved Aperture System Combined With A High Pressure Gas Beam Stop," filed Nov. 1, 2001, incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to neutron radiography, and more specifically, it relates to rotating aperture systems for use in high-energy neutron imaging applications.

2. Description of Related Art

Conventional rotating aperture systems for use in neutron radiography use close tolerances so the rotor and stator are in close proximity but non-contacting during rotation. This leaves a small, but definite leakage path for gas to escape through the aperture system when it is closed.

Stopping a 7 MeV, >50 $\mu$A average current deuterium beam on a solid target requires angled or rotating target systems that are water cooled since the power density in the beam is >120 kW. This tends to put a large amount of material in the path of the neutron beam and would produce shadows on the object image and adversely impact interpretation of the image.

Stopping a deuterium beam with a solid beam stop will implant deuterium in the solid that will begin to produce background (off-energy) neutrons which will decrease the resolution and contrast in a neutron image.

The main way leakage has been addressed by others is to just accept it and use large pumps to keep the pressures low in the differential pumping section of the system, by using foils across the holes if the beam power is low enough, or to limit the pressure in the gas cell.

Beam powers used to date have been low enough that solid or rotating-disk beam stops have been acceptable. In addition, since users have thus far not been interested in high-resolution radiographs and images of objects, shadows produced by the beam stop were not important.

Most users to date are less concerned with having a purely monoenergetic neutron beam since they are doing "binary radiography", i.e., they are looking to see if something is there or not, so stopping the beam on a solid is perfectly acceptable.

By exploring the approach of moving a neutral gas rapidly across the beam path by exploiting the pressure drop in a venturi, it appears that nominal gas density can be maintained in front of the beam since the region of rarefaction due to beam heating rapidly moves away from the beam focus channel carried by the momentum of the mass flow.

Others have tried to combat rarefaction by physically moving a large enclosed volume of gas rapidly in front of a particle beam. Another approach is to try and pre-cool the gas in the gas cell before the beam impinges, so the amount of time it takes for the density to drop is slightly increased, though this effect would improve the time-integrated neutron yield only slightly.

It is desirable to improve the sealing performance of the turbulent volume gas cell aperture system. It is also desirable to address problems associated with gas rarefaction and de-densification due to the particle beam impinging on and depositing energy in the neutral gas in the gas cell. It is further desirable to improve and extend the operating range of a "windowless" rotating aperture system.

SUMMARY OF THE INVENTION

It is an object of the present invention to provide a combination of design improvements to significantly improve and extend the operating range of a "windowless" rotating aperture system.

It is another object of the present invention to provide a combination of design improvements with a novel beam stopping technology to further improve and extend the operating range of a "windowless" rotating aperture concept.

These and other objects will be apparent to those skilled in the art based on the teachings herein.

The design changes described here were initiated to improve the sealing performance of the turbulent volume gas cell aperture system by:

(1) using a very rigid rotor and stator assembly to allow very close tolerances to be held at up to 4000 RPM;

(2) having the rotor surface seal from the high-pressure side to the lowpressure side so the pressure gradient augments the closure seal; and (3) using special materials attached to the sliding surface of the rotor that will allow lapping of the rotor into the stator surfaces in order to achieve extremely close tolerances which result in an improved seal.

To address problems associated with gas rarefaction and de-densification due to the particle beam impinging on and depositing energy in the neutral gas in the gas cell, further design changes were initiated to improve the neutron production efficiency in the gas cell:

1. A venturi tube was placed between two rotors in which the deuterium gas is passed perpendicular to the beam at a high velocity driven by a pressure drop across the venturi.

2. In the rotor assemblies, baffle plates were designed to damp the sonic shock wave of gas escaping from the gas cell into the vacuum, and to provide a localized region of slightly higher pressure to impede the shock propagation.

3. To decrease the deflection and vibration due to the force change that occurs when the aperture opens and closes, 2–4 additional holes that are not aligned with the rotor aperture would be used to provide a more uniform background pressure such that the transient pressure due to the beam aperture holes opening and closing is now a fraction of the total pressure.

To extend the range of operational beam powers, a high-pressure, high atomic number (Z), gas beam stop was added to the rotating aperture design concept in one embodiment This beam stop will stop deuterium beams of 50–400 $\mu$A average current in a gas rather than a solid. Such a design removes the problem of having implanted deuterium in a solid beam stop which leads to energy broadening due to off-energy neutrons in the resultant neutron beam and higher backgrounds due to scattered neutrons. It also mitigates the problem of dissipating the peak power in the beam, as the energy is deposited in a distributed fashion as the beam slows in the gas. From an imaging standpoint, the gas beam stop also minimizes attenuation of the desired neutron beam which leads to cleaner images.

Lawrence Livermore National Laboratory (LLNL) plans on using this improved rotating aperture system and method of stopping the deuterium beam for a high resolution, accelerator-driven neutron imaging system. This invention would also be of use to anyone using 5–20 MeV beams with average currents in excess of 20 $\mu$A who wants to work around the disadvantages of stopping the beam on a solid surface.

High-energy neutron imaging is still a relatively new area of research. It is reasonable to assume that as neutron imaging becomes more accepted as a non-destructive inspection tool, the need for robust rotating aperture targets with low-attenuation, self-healing beam stops could increase dramatically. While the current applications for high-energy neutron imaging are still rather specialized, the field is expanding and there may well be significant commercial applications for this new technology. The needs of the Enhanced Surveillance Campaign at LLNL have provided the current impetus to design and build a high-intensity, high-resolution neutron imaging system which will be unique in the world. As such, it is anticipated that as the system is developed, and as results start to be produced, more applications will become apparent which call upon the strength of this technique, e.g., for imaging low-z materials, voids, and inclusions which are heavily shielded by high-Z materials.

As of today, some of the applications that could benefit from neutron imaging would be:

1. Inspection of large metal ingots for voids and inclusions (steel and aluminum manufacturing).
2. Inspection of tree trunks looking for cracks, voids, and metal inclusions before cutting (a large dollar, low-tech industry).
3. Imaging bridge abutments and concrete structural pillars for voids and cracking.
4. Imaging and interrogating trucks and cargo containers.
5. Providing a small-source-spot neutron beam that has a spatially dependent energy distribution dependent on angle for neutron resonance radiography applications for discriminating common materials.

DETAILED DESCRIPTION OF THE INVENTION

Rotating Aperture System— Turbulent Volume Gas Cell

The improvements to the rotating aperture system described here were conceived and implemented to enhance the sealing performance, neutron production rate, longevity, radiation hardness, and reliability over the design concept originally put forth in the literature. These improvements include:

1. The sealing around the discs is improved by using a non-galling material and effectively lapping the rotor and the stator. Doing this, minimal separation is achievable between the rotor and stator which should provide maximum sealing for a closed condition. This material is a soft ceramic such as boron nitride that will conformally lap when it comes in contact with a metal surface.

2. The aperture system was designed so the rotors would seal from the higher-pressure to the lower pressure side of the aperture, thus enabling the pressure gradient to help seal the aperture. The design of the shaft on tapered bearings allowed the rotor to be precision fit onto the stator assembly so the original parts could be contact fit run to get lapped in, disassembled, cleaned, and precision reassembled for very tight tolerance fitting to minimize gas leakage when the rotor is in a sealed position.

3. The high-pressure pumping stage includes a centrifugal impeller which serves to sweep the 0.5–5 Torr deuterium gas that does leak into this stage out through the two pumping ports shown.

4. The rotor drive shaft is coming in from the low-radiation side of the assembly to improve reliability of the motor, bearings, and rotating vacuum seal.

Figure 1:
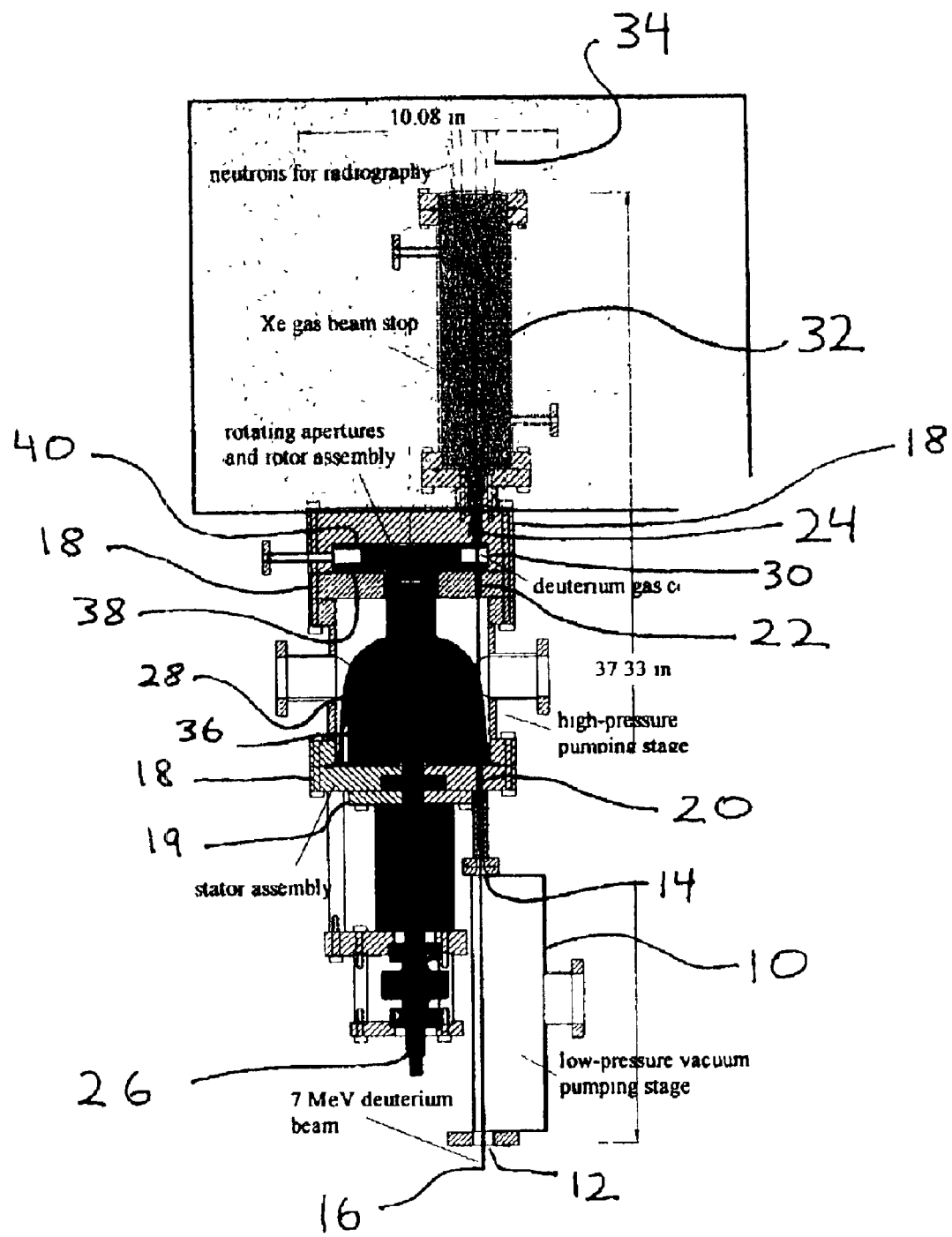
FIG. 1 is an end station drawing and shows the high and low pressure pumping stages, rotating aperture rotor assembly, stator assembly, pressurized gas cell and beam stop concept for the turbulent volume approach.

FIG. 1 is an end station drawing and shows the high and low pressure pumping stages, rotating aperture rotor assembly, stator assembly, pressurized gas cell and beam stop concept. The system includes a low-pressure vacuum pumping stage 10 with apertures 12 and 14 for passage of a deuterium beam 16. A stator assembly 18 includes holes 20, 22 and 24 for passage of the beam. The rotor assembly includes a shaft 26 connected to a centrifugal gas impeller 28 and a deuterium gas cell 30. The gas cell 30 includes a single hole on each side of the cell that together align with holes 22 and 24 every rotation. The rotating holes of the gas cell are synchronized with the firing of the deuterium beam such that the beam only fires when a clear aperture exists through apertures 12 and 14 and through holes 20, 22 and 24. Once fired, the beam passes through the D2 gas cell, where neutrons usable for radiography 34 are produced via a $D(d,n)^3He$ reaction, then into the Xe gas beam stop 32. Portions 36, 38 and 40 of the rotor are lapped against the stator to improve the sealing surfaces, to prevent rapid escape of the deuterium gas from the gas cell 30.

High Pressure Gas Beam Stop

After the deuteron beam passes through the gas cell, it needs to be disposed of in such a way that the energy distribution of neutrons generated in the gas cell is minimally impacted. Conventional approaches for stopping a 7-MeV, 100–300 $\mu$A average-current deuteron beam involve impinging the beam either on a rotating disk or on a thin watercooled metal target sloped to decrease the power density. Both of these approaches require that significant hardware must be placed in the flight path of the neutrons generated in the gas cell which would adversely affect the energy distribution of the neutron beam.

The beam stop approach shown in FIG. 1 is simple, inexpensive, and causes minimal disruption to the neutron beam. The beam is stopped in a high-Z, high-pressure gas directly behind the deuterium gas cell. The last rotor on the rotating aperture is used to minimize the amount of mixing between the two gases. This approach allows the deuterium gas cell to be a short length, which is needed for high resolution by keeping the interaction region small, and it helps keep the neutrons nearly monoenergetic, as a small energy spread is imparted on the beam as it passes through the deuterium gas cell. The 1–3 kW of average beam power would be removed by a heat exchanger in the high-Z gas recirculation loop.

An embodiment of the present design uses xenon for the high-Z gas as it has a high atomic number which increases the stopping power of the gas, it lies below the Coulomb barrier for nuclear interactions with incoming deuterium at 7 MeV, and it has a reasonably low cross section for fast neutrons. By using xenon as a stopping gas, maintaining the purity of the different gas streams in the gas cell and beam stop would be accomplished by taking advantage of the property differences between the two gases. Deuterium in the xenon gas could be removed by a palladium filter which takes advantage of the difference in mobility of the two species in the metal, and xenon atoms in the deuterium could be removed by cryo-trapping which is facilitated by the drastically different condensation temperatures.

The other benefits of using a gas beam stop are that the problem of getting lower-energy background neutrons from the implanted deuterium in the stop is mitigated and the whole area of radiation damage in a solid material is avoided.

Some specific benefits of using a high-pressure gas beam stop include, improved longevity, radiation hardness, and reliability over the design concept put forth in the literature. These improvements include:

1. For the high-resolution imaging machine proposed, the beam brightness is high enough that even a rotating beam stop is problematic as the beam would need to hit it at a grazing-incidence to get the power density low enough that material is not ablated off the surface. In addition, putting such a massive rotating mechanical device in the path of the neutron beam would produce a shadow on the image of the object of interest, it would lower the neutron beam intensity, and it would lead to scattered neutrons that would degrade the image resolution.

2. For high-resolution imaging, off-energy background neutrons dilute the image contrast and resolution. By using a gas beam stop, the background neutrons that would come from implanted deuterium are minimized.

3. The space where the beam impinges on the stop is naturally self-healing as it is a gas. Calculations indicate that the hydrodynamic relaxation time is such that any channel de-densification heals by the time the next beam pulse comes arrives.

Rotating Aperture System—Cross Flow Venturi Gas Cell

Figure 2:
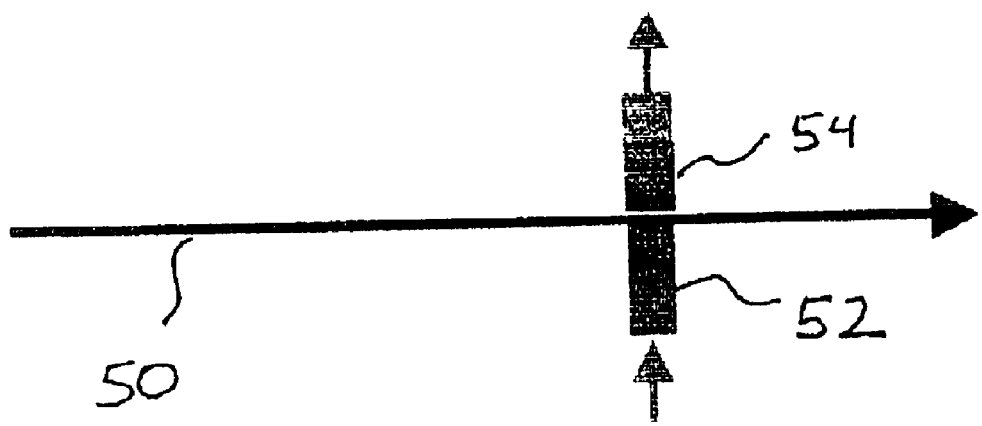
FIG. 2 show that the flow rate effectively moves cold gas into the beam channel and hot expanding gas out of the beam channel so the de-densification effect is minimized.

As the >100 kW of peak power in the beam macrobunch deposits up to 10 kW of power in the neutral gas as the beam interacts with it, significant gas heating occurs which leads to an appreciable de-densification or rarefaction of the target gas occurring on the order of 10s of microseconds for the power levels indicated. To minimize the effect of this rarefaction, the neutral gas column is moved transversely across the beam path at 200–300 m/sec. As shown in FIG. 2, this flow rate effectively moves cold gas into the beam channel and hot expanding gas out of the beam channel so the de-densification effect is minimized. The figure illustrates a particle beam 50 directed through an ambient temperature high-density deuterium gas 52, which is flowing past the beam 50 at 100–300 m/sec. In a region 54 past the point of intersection between the particle beam 50 and the gas 52, the gas becomes heated by the beam and is converted to a low-density deuterium gas.

To address concerns about gas rarefaction in the deuterium gas cell due to the high power in the macrobunches of the pulsed deuterium beam, of holding alignment in the rotating parts of the system, and of needing a ferrofluidic vacuum seal, the present invention includes the following improved embodiments:

1. The rotors, shaft, bearings, motor, and stator assembly are mounted on a rigid precision mounting frame that is independent of the vacuum/pressure envelope of the system.

2. The motor is installed inside the vacuum canister.

3. The high pressure deuterium gas in the gas cell is moved at high speeds across the particle beam path using a gas venturi (also herein referred to as a crossflow venturi) tube to create a fast moving gas column moving out of a high pressure gas reservoir driven by a pressure drop.

4. To damp out the gas shock wave moving from the high-pressure gas cell into the vacuum space, the rotor assemblies have been designed with internal plates that act as baffles. These baffles will improve the efficiency of the rotating aperture seal by providing a flow impedance to the shock due to a region of localized higher pressure that would exist in the baffles.

The design improvements listed here improve the brightness, reliability, and beam-to-neutron conversion efficiency of the rotating aperture source design by improving the rigidity and tolerances in the rotating machinery and by significantly reducing the gas rarefaction that would occur in quasi-static deuterium gas due to the high power of the beam.

These improvements could also be useful for any application that requires maintaining a high-pressure gradient over a short distance between a gas and a vacuum, or for an application that requires placing a localized region of high-pressure gas inside of a vacuum system. Some examples of these types of applications are:

1. Using a rotating aperture shutter instead of beam windows to isolate a high-power beam target (spallation neutron sources, subcritical reactor assemblies, sub-atomic production targets) environments from the accelerator vacuum to mitigate potential damage and lost operational time due to target outgassing, sputtering, and failure.

2. Using rotating apertures to contain localized regions of high pressure gas in a vacuum environment, such as gas strippers in heavy ion accelerators or gas attenuators for intense SASE (self-amplified stimulated emission) coherent light sources and free electron lasers.

3. Creating dynamic portals between vacuum and atmosphere, where pulsed particle beams can pass from the vacuum environment of the accelerator to either atmosphere, or into a process gas that supports nuclear reactions, nuclear transmutation processes, or other beam-gas interactions.

4. Using the rotating aperture system to physically isolate beamline components from interaction chambers and to damp shock waves and block debris from dynamic radiography targets.

Figure 3:
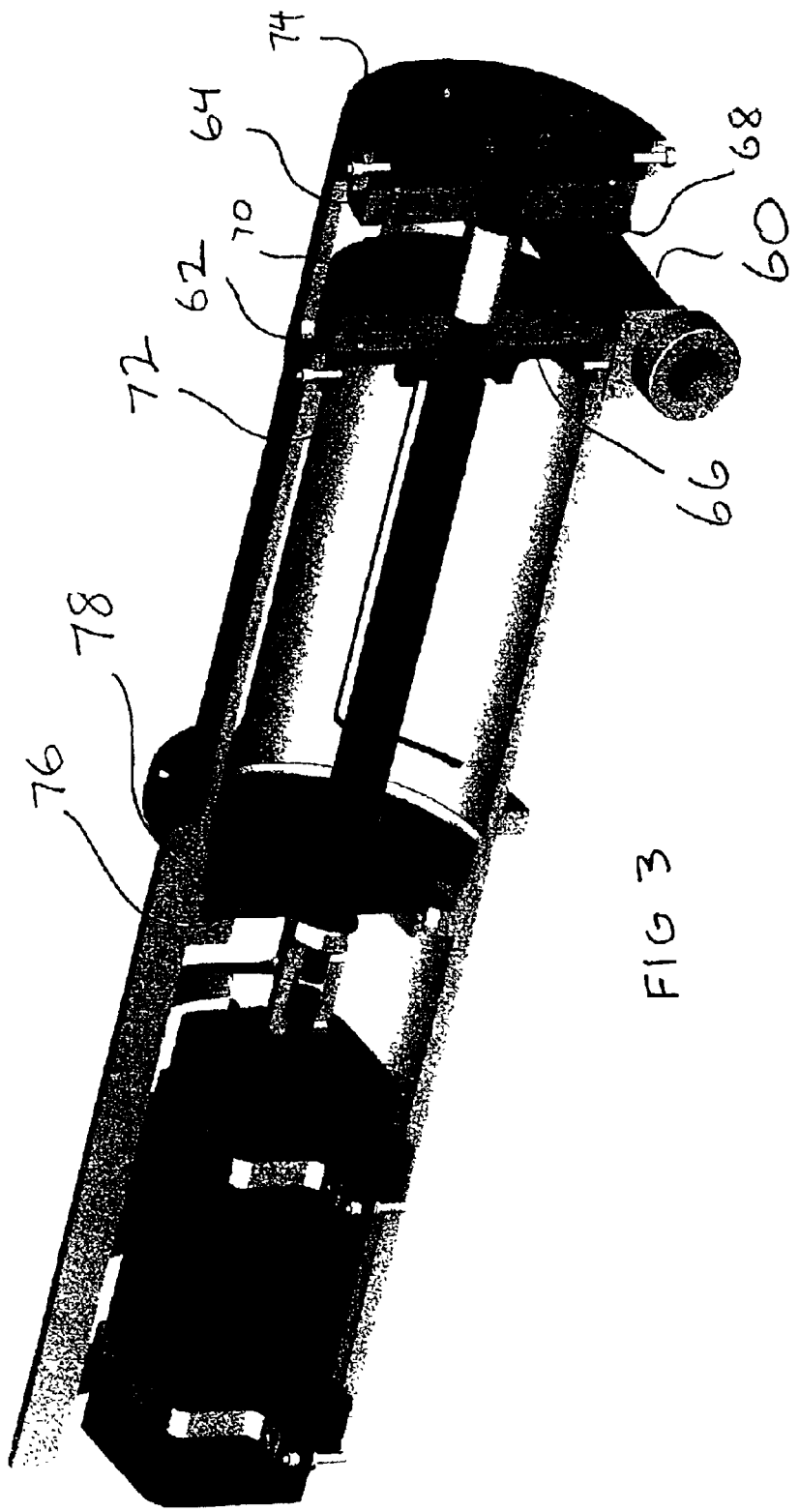
FIG. 3 shows an alternate design to the rotating gas cell where a venturi tube is located between two baffled rotors for the cross flow venture approach.

FIG. 3 shows an alternate design to the rotating gas cell where a venturi tube 60 is located between two baffled rotors 62, and 64, which are spinning at about 4000 RPM in one embodiment. The crossflow venturi tube contains the gas flow and develops high fluid flow velocities that are driven by a pressure drop across the venturi. The venturi tube is made of aluminum in one embodiment, and includes a hole on each side adjacent to the rotating baffled rotors to provide an aperture for the deuterium beam. Washer type structures 66 and 68 are affixed to the venturi tube 60 such that the holes in the washers align with the holes in the venturi tube. To help contain the gas, the spacing between the venturi tube and the rotors is designed to be less than 0.005". The rotors 62 and 64 are designed with internal baffling 70 to damp the shock wave that will come from the high-pressure gas cell when the apertures coincide to create the "beam open" condition. As discussed above, when the aperture holes in the baffled rotors align with the aperture holes in the venturi tube, the deuterium beam is passed through the apertures. The figure further shows a first stator 72 adjacent to rotor 62, a second stator 74 adjacent to rotor 64 and third rotor 76 adjacent to a third stator 78, each having holes that align with the beam path and the apertures in the venturi tube. In one embodiment, the pressure within the venturi tube is about 3 atm. The pressure in the holes in rotor 62 and stator 72 are at a lower pressure than that of the venturi tube (~10 Torr). The pressure in the holes of the third rotor 76 and the third stator 78 are at a lower pressure that the pressure in the holes in rotor 62 and stator 72 (~$10^{-5}$ Torr).

The combination of the very tight tolerance between the rotors and stators, the pressure transients that would come from the high-pressure gas cell every time the aperture opened, and the possible thermal and vibrational environment that would exist for this piece of rotating machinery necessitates the frame that hold the rotating components be very rigid. To minimize the impact of temperature variations, the spacing between the closest-tolerance components is kept at a minimum.

To decouple any forces from pressure or fabrication errors in the vacuum vessel, the frame is connected to the vacuum vessel at the midpoint of the assembly. The vacuum vessel is thereby allowed to move and be out of alignment to standard tolerances without affecting the critical alignment of the rotors. As the motor is mounted in the vacuum space to eliminate the need for some sort of high-speed vacuum feedthrough like a ferrofluidic seal, consideration must be given to removing the dissipated heat in the motor. In the design being developed, the heat will be conducted out of the vacuum environment by aluminum strapping that would connect the motor to the aluminum vacuum case where it can then be transferred to ambient air.

The present invention does not preclude the use of a high-pressure gas beam stop, as the vacuum vessel can be designed to seal and contain the high pressure gas charge (shown above). This approach of having a rotating aperture can also be used as a system to seal a vacuum system against atmosphere, where the flange with the aperture leading to the atmospheric environment would replace the crossflow venturi assembly.

The combination of a cross-flow venturi to rapidly move gas across the beam focus channel, of using a baffled rotor to damp the shock wave that occurs when the apertures coincide and a high pressure gas pulse moves into the vacuum chamber, of the motor inside the vacuum case, and of having a rigid precision frame for the rotating machinery that is independent of the vacuum housing makes this design concept unique in its application of varying techniques to achieve a high-brightness neutron source.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated. The scope of the invention is to be defined by the following claims.

We claim:

1. A rotating aperture system, comprising:
    an input rotor with an input rotor aperture and an output rotor with a output rotor aperture, wherein said input rotor aperture and said output rotor aperture are configured to simultaneously align with a beam path at a position of rotation of said input rotor and said output rotor; and
    means for moving a volume of gas across said beam path, wherein said means are located between said input rotor and said output rotor, wherein said means has a beam entry aperture and a beam exit aperture aligned with said beam path and said position of rotation.

2. The rotating aperture system of claim 1, wherein said means for moving a volume of gas across said beam path is selected from the group consisting of a gas venturi tube and a moving gas cell.

3. The rotating aperture system of claim 1, wherein said beam path is configured for passage of a beam selected from the group consisting of a deuterium beam, a neutron beam, a sub-atomic particle beam, a heavy ion beam, a beam of electromagnetic radiation and a particle beam.

4. The rotating aperture system of claim 1, further comprising means for generating a beam for propagation along said beam path, wherein said means for generating a beam is selected from the group consisting of means for generating a deuterium beam, means for generating a neutron beam, means for generating a sub-atomic particle beam, means for generating a heavy ion beam, means for generating a beam of electromagnetic radiation and means for generating a particle beam.

5. The rotating aperture system of claim 1, wherein said gas comprises deuterium gas.

6. The rotating aperture system of claim 1, further comprising means for rotating said input rotor and said output rotor such that said input rotor aperture and said output rotor aperture simultaneously align with said beam path and said beam entry aperture and said beam exit aperture.

7. The rotating aperture system of claim 6, wherein said input rotor comprises at least one baffle to damp out gas shock waves.

8. The rotating aperture system of claim 6, wherein said output rotor comprises at least one baffle to damp out gas shock waves.

9. The rotating aperture system of claim 2, wherein said gas venturi tube comprises aluminum.

10. The rotating aperture system of claim 2, further comprising a first shock absorbing disc fixedly connected to said gas venturi tube and having an aperture aligned with said beam entry aperture of said gas venturi tube.

11. The rotating aperture system of claim 2, further comprising a second shock absorbing disc fixedly connected to said gas venturi tube and having an aperture aligned with said beam exit aperture of said gas venturi tube.

12. The rotating aperture system of claim 1, further comprising a mounting frame and a first stator fixedly attached to said mounting frame and located adjacent to said input rotor on the side of said input rotor that is opposite from the side of said input rotor that said beam entry aperture of said means for moving a volume of gas is located, wherein said first stator comprises a first hole aligned with said beam path.

13. The rotating aperture system of claim 12, wherein said input rotor is lapped into said first stator to reduce gas leakage from said means for moving a volume of gas.

14. The rotating aperture system of claim 13, wherein said input rotor comprises a ceramic that will conformally lap when it comes in contact with a metal surface.

15. The rotating aperture system of claim 14, wherein said ceramic comprises boron nitride.

16. The rotating aperture system of claim 12, further comprising a second stator fixedly attached to said mounting frame and located adjacent to said output rotor on the side of said output rotor that is opposite from said beam exit aperture of said means for moving a volume of gas, wherein said second stator comprises a second hole aligned with said beam path.

17. The rotating aperture system of claim 16, wherein said exit rotor is lapped into said second stator to reduce gas leakage from said means for moving a volume of gas.

18. The rotating aperture system of claim 17, further comprising a gas beam stop fixedly connected to said second stator and aligned with said beam path.

19. The rotating aperture system of claim 18, wherein said gas beam stop comprises a high-Z gas.

20. The rotating aperture system of claim 19, further comprising a heat exchanger operatively connected to said gas beam stop to reduce the heat within said high-Z gas.

21. The rotating aperture system of claim 19, wherein said high-Z gas comprises Xenon.

22. The rotating aperture system of claim 19, further comprising a palladium filter operatively placed within said beam stop to remove deuterium from said high-Z gas.

23. The rotating aperture system of claim 19, further comprising a cryo-trap operatively connected to said gas beam stop to remove Xenon atoms from said deuterium gas.

24. The rotating aperture system of claim 16, further comprising a third stator fixedly attached to said mounting frame and located within said frame in a spaced relationship relative to said first stator and on the opposite side of said first stator than said second stator, wherein said third stator comprises a third hole aligned with said beam path, said rotating aperture system further comprising a second input rotor with a second input rotor aperture, wherein said second input rotor is adjacent to said third stator and on the side of said third stator opposite from said first stator, wherein said second input rotor is configured to simultaneously align with said beam path at said position of rotation, said rotating aperture system further comprising a first vacuum system operatively connected to a vacuum vessel surrounding said mounting frame to provide a lower relative pressure within said input rotor aperture and said input stator aperture relative to said means for moving a volume of gas, said rotating aperture system further comprising a second vacuum system operatively connected to provide a lower relative pressure within said second input rotor aperture and said third stator aperture relative to said lower relative pressure within said input rotor aperture and said input stator aperture.

25. The rotating aperture system of claim 24, further comprising a centrifugal impeller located between said first stator and said third stator and driven by means for rotating said input rotor and output rotor, wherein said centrifugal impeller is designed to sweep out deuterium gas that does leak from said means for moving a volume of deuterium gas across said beam path into the area between said first stator and said third stator.

26. The rotating aperture system of claim 6, wherein said means for rotating said input rotor and said output rotor comprises a motor connected to rotate a shaft.

27. The rotating aperture system of claim 26, wherein said motor is located on said input rotor side of said means for moving a volume of gas.

28. The rotating aperture system of claim 12, further comprising a vacuum vessel, wherein said mounting frame is within said vacuum vessel.

29. The rotating aperture system of claim 1, wherein the spacing between said means for moving a volume of gas and said input rotor is less than 0.005" and wherein the spacing between said means for moving a volume of gas and said output rotor is less than 0.005".

30. The rotating aperture system of claim 12, wherein said frame is connected to a pressurizing pumping stage at about the midpoint of said frame assembly.

31. A method for rotating an aperture to a moving volume of gas, comprising. rotating an input rotor having a input rotor aperture;

rotating an output rotor with a output rotor aperture, wherein said input rotor aperture and said output rotor aperture are configured to simultaneously align with a beam path at a position of rotation of said input rotor and said output rotor; and moving a volume of gas across said beam path, wherein said means are located between said input rotor and said output rotor, wherein said means has a beam entry aperture and a beam exit aperture aligned with said beam path and said position of rotation.

32. The method of claim 31, wherein the step of moving a volume of gas across said beam path is carried out with means for moving a volume of gas, wherein said means are selected from the group consisting of a gas venturi tube and a moving gas cell.

33. The method of claim 31, further comprising generating a beam for propagation along said beam path using means for generating a beam selected from the group consisting of means for generating a deuterium beam, means for generating a neutron beam, means for generating a sub-atomic particle beam, means for generating a heavy ion beam, means for generating a beam of electromagnetic radiation and means for generating a particle beam.

34. The method of claim 31, wherein the step of moving a volume of gas across said beam path includes moving deuterium gas.

35. The method of claim 31, further rotating said input rotor and said output rotor such that said input rotor aperture and said output rotor aperture simultaneously align with said beam path and said beam entry aperture and said beam exit aperture.

36. The method of claim 31, further comprising damping out gas shock waves with at least one baffle located in at least one rotor selected from the group consisting of said input rotor and said output rotor.

37. The method of claim 32, further absorbing shocks to said gas venturi tube with a shock absorbing disc selected from the group consisting of (i) a first shock absorbing disc fixedly connected to said gas venturi tube and having an aperture aligned with said beam entry aperture and (ii) a second shock absorbing disc fixedly connected to said gas venturi tube and having an aperture aligned with said beam exit aperture.

38. The method of claim 31, further comprising fixedly mounting a first stator to a frame, wherein said first stator is located adjacent to said input rotor on the side of said input rotor that is opposite from the side of said input rotor that said beam entry aperture of said means for moving a volume of gas is located, wherein said first stator comprises a hole aligned with said beam path.

39. The method of claim 38, further comprising lapping said input rotor into said first stator.

40. The method of claim 38, further comprising fixedly mounting a second stator to said frame, wherein said second stator is located adjacent to said output rotor on the side of said output rotor that is opposite from said beam exit aperture of said means for moving a volume of gas, wherein said second stator comprises a hole aligned with said beam path.

41. The method of claim 40, further comprising lapping said exit rotor into said second stator.

42. The method of claim 40, further comprising connecting a gas beam stop to said second stator and aligned with said beam path.

43. The method of claim 42, further comprising reducing the heat within the gas within said gas beam stop with a heat exchanger operatively connected to said gas beam stop.

44. The method claim 40, further comprising removing deuterium from the gas within said gas beam stop with a palladium filter operatively placed within said beam stop.

45. The method of claim 42, further comprising removing Xenon atoms from the gas within said gas beam stop with a cryo-trap operatively connected to said gas beam stop.

46. The method of claim 40, further comprising mounting a third stator to said frame, wherein said third stator is located within said frame in a spaced relationship relative to said first stator and on the opposite side of said first stator than said second stator, wherein said third stator comprises a third hole aligned with said beam path, said rotating aperture system further comprising a second input rotor with a second input rotor aperture, wherein said second input rotor is adjacent to said third stator and on the side of said third stator opposite from said first stator, wherein said second input rotor is configured to simultaneously align with said beam path at said position of rotation, said rotating aperture system further comprising a first vacuum system operatively connected to a vacuum vessel surrounding said mounting frame to provide a lower relative pressure within said input rotor aperture and said input stator aperture relative to said means for moving a volume of gas, said rotating aperture system further comprising a second vacuum system operatively connected to provide a lower relative pressure within said second input rotor aperture and said third stator aperture relative to said lower relative pressure within said input rotor aperture and said input stator aperture.

47. The method of claim 38, further comprising locating said frame vessel.

* * * * *